US011667977B2

(12) United States Patent
Schrezenmeir et al.

(10) Patent No.: US 11,667,977 B2
(45) Date of Patent: Jun. 6, 2023

(54) METHOD OF USING A MEDICATION OR A FOOD SUPPLEMENT WITH LACTOBACILLUS STRAINS ISOLATED FROM KIMERE FOR STRENGTHINING THE IMMUNE SYSTEM

(71) Applicants: Jurgen Schrezenmeir, Karlsruhe (DE); Knut Heller, Kiel (DE)

(72) Inventors: Jurgen Schrezenmeir, Karlsruhe (DE); Knut Heller, Kiel (DE)

(*) Notice: Subject to any disclaimer, the term of this patent is extended or adjusted under 35 U.S.C. 154(b) by 0 days.

(21) Appl. No.: 14/708,942

(22) Filed: May 11, 2015

(65) Prior Publication Data

US 2016/0074442 A1    Mar. 17, 2016

Related U.S. Application Data

(62) Division of application No. 13/390,210, filed as application No. PCT/DE2010/000953 on Aug. 11, 2010, now abandoned.

(30) Foreign Application Priority Data

Aug. 11, 2009 (DE) .......................... 102009037089.7

(51) Int. Cl.
| | |
|---|---|
| *A61P 9/12* | (2006.01) |
| *C12Q 1/689* | (2018.01) |
| *A23L 33/135* | (2016.01) |
| *A61K 35/747* | (2015.01) |

(52) U.S. Cl.
CPC .......... *C12Q 1/689* (2013.01); *A23L 33/135* (2016.08); *A61K 35/747* (2013.01); *A23V 2002/00* (2013.01); *A23Y 2220/35* (2013.01); *A23Y 2220/67* (2013.01)

(58) Field of Classification Search
CPC ............. A23L 33/135; A23Y 2220/35; A23Y 2220/67; A61P 37/00; A61P 1/00; A61P 1/04; A61P 1/12; A61P 3/00; A61P 3/06; A61P 3/10; A61P 5/16; A61P 5/48; A61P 9/10; A61P 9/12; A61P 11/06; A61P 17/00; A61P 17/06; A61P 19/04; A61P 21/04; A61P 25/00; A61P 29/00; A61P 31/00; A61P 31/10; A61P 31/18; A61P 37/08; A61P 11/00; A61P 19/02; A61P 27/02; A61P 31/06; A23V 2002/00; A61K 35/747; C12Q 1/689
See application file for complete search history.

(56) References Cited

U.S. PATENT DOCUMENTS

| 4,473,452 A | 9/1984 | Cantor et al. |
| 2006/0083723 A1 | 4/2006 | Ching-Hsiang et al. |
| 2006/0182727 A1 | 8/2006 | Yamahira et al. |

FOREIGN PATENT DOCUMENTS

| KR | 2004/0068820 A | 3/2006 |
| KR | 100742900 B1 | 7/2007 |
| WO | 02/34273 A1 | 5/2002 |
| WO | 03/022255 A2 | 3/2003 |
| WO | 2008/060198 A1 | 5/2008 |
| WO | 2008/064521 A1 | 6/2008 |
| WO | 2008/079009 A1 | 7/2008 |
| WO | 2009/068474 A1 | 6/2009 |

OTHER PUBLICATIONS

Mikelsaar et al., Microbial Ecology in Health and Disease. 2009; 21: 1-27).*
Molecular Characterization and Probiotic Potential of Kimere Lactobacilli (English) Taschenbuch—Jul. 24, 2009 von Patrisio Njeru (Autor), 2009, Dissertation.*
Maassen et al. Strain-dependent induction of cytokine profiles in the gut by orally administered Lactobacillus strains, Vaccine, vol. 18, p. 2613-2623 (Year: 2000).*
International Preliminary Report on Patentability for PCT Application No. PCT/DE2010/000953, dated Feb. 16, 2012, 12 pages.
Njeru et al., Aktuel Ernahrungsmed 2007; 32-P3_6.
Njeru, P., Master's thesis (2009), Abstract.
Herias et al., Clin Exp Immunol 1999; 116:283-290.

\* cited by examiner

*Primary Examiner* — Taeyoon Kim
*Assistant Examiner* — Tiffany M Gough
(74) *Attorney, Agent, or Firm* — DP IP Group; Franco S. De Liguori

(57) ABSTRACT

The invention relates to a pharmaceutical and/or dietetic composition for increasing the impact of the immune defense of higher living beings, wherein bacteria of the species *Lactobacillus fermentum* from at least one of the strains K1-Lb1 or K1-Lb6 or K2-Lb4 or K6-Lb4 or K7-Lb1 or K8-Lb1 or K9-Lb6 are contained in order to control the adaptive and natural immune defense by means of T helper 1 and T helper 2 cells and/or bacteria of the species *Lactobacillus fermentum* from at least one of the strains K2-Lb6 or K11-Lb3 are contained in order to strengthen the native immune defense.

4 Claims, 10 Drawing Sheets
Specification includes a Sequence Listing.

Properties of the Bacterial Strains

| Property | Kx-Lby Designation | | | | | | | | | |
|---|---|---|---|---|---|---|---|---|---|---|
| | Lb1 | K1-Lb6 | K2-Lb4 | Lb6 | K4-Lb6 | Lb4 | Lb1 | Lb1 | Lb3 | K11-L3 |
| Bile salt tolerance | + | + | + | + | +++ | + | + | + | + | |
| pH tolerance | | ++ | + | + | ++ | + | +++ | +++ | ++ | |
| Th1 helper reaction, Th2 influence reduced | + | + | + | | + | | | | | |
| Th2 response strengthened, Th1 influence reduced | | | | | | + | + | + | | |
| Defensin release | | | | ++ | | | | | | +++ |

FIG. 1

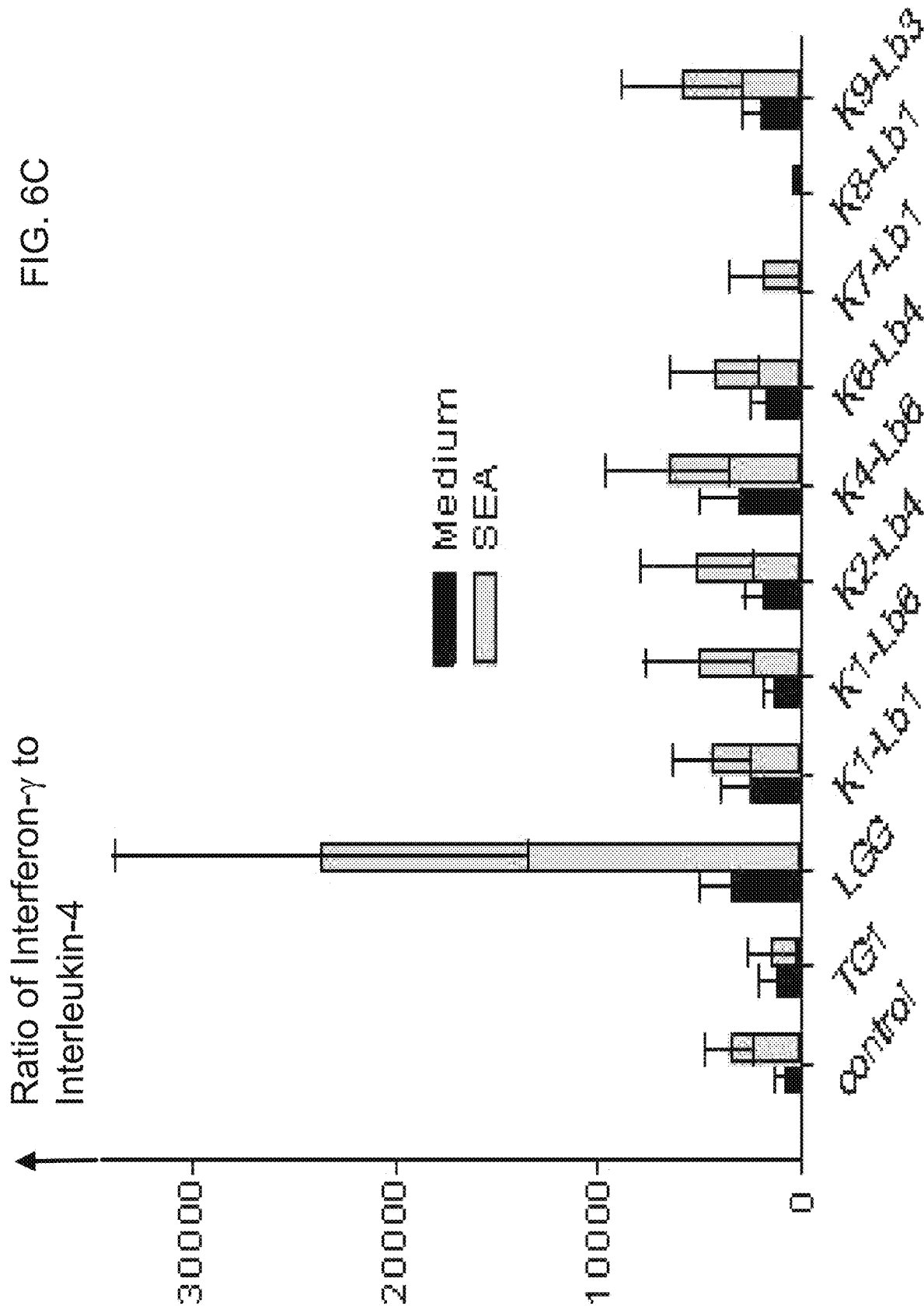

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: forward primer UP68

<400> SEQUENCE: 1
tggctcagat tgaacgctgg cggc                                          24

<210> SEQ ID NO 2
<211> LENGTH: 21
<212> TYPE: DNA
<213> ORGANISM: Artificial Sequence
<220> FEATURE:
<223> OTHER INFORMATION: reverse primer UP69

<400> SEQUENCE: 2
cctttccctc acggtactgg t                                             21

<210> SEQ ID NO 3
<211> LENGTH: 20
<212> TYPE: DNA
<213> ORGANISM: Artificial Sequence
<220> FEATURE:
<223> OTHER INFORMATION: forward primer LF1

<400> SEQUENCE: 3
aataccgcat tacaactttg                                               20

<210> SEQ ID NO 4
<211> LENGTH: 20
<212> TYPE: DNA
<213> ORGANISM: Artificial Sequence
<220> FEATURE:
<223> OTHER INFORMATION: reverse primer LF2

<400> SEQUENCE: 4
ggttaaatac cgtcaacgta                                               20
```

METHOD OF USING A MEDICATION OR A FOOD SUPPLEMENT WITH LACTOBACILLUS STRAINS ISOLATED FROM KIMERE FOR STRENGTHINING THE IMMUNE SYSTEM

CROSS-REFERENCE TO RELATED APPLICATION

This Application is a divisional of and claims priority to U.S. patent application Ser. No. 13/390,210, filed Apr. 23, 2012, which is a Section 371 National Stage Application of International Application No. PCT/DE2010/000953 filed Aug. 11, 2010 and published as WO 2011/018080 A2 on Feb. 17, 2011, in German, which claims priority to German patent application Serial No. 10 2009 037 089.7, filed Aug. 11, 2009, the contents of which are hereby incorporated by reference in their entirety.

The invention relates to a pharmaceutical and/or dietetic composition for strengthening the effect of the human immune defence.

The immune defence is an ever present and active biological defence system of higher living organisms, which prevents tissue damage by pathogens. It consists of various organs as well as cells and molecules of various types that form a complex network. It eliminates microorganisms and other foreign substances that have penetrated into the body and is also capable of destroying the body's own cells that have become defective. The immune defence has great importance for the physical intactness of living organisms, since virtually all organisms are continually subject to the influences of the living environment, of which some even pose an existential threat.

If harmful microorganisms penetrate into the body, this can lead to functional disturbances and illness. Typical pathogens are bacteria, viruses and fungi as well as single-cell parasites, for example protozoa or other plasmodia, or multicellular parasites, such as tapeworms.

Currently new genera of harmful bacteria and other unwelcome microorganism are increasingly growing up, which are resistant not only to one but often even to a plurality of medicines, which are still very effective against the genera known hitherto. A threatening example in July 2009 is the pathogen N1H1, also known as swine flu, the mutants of which could lead to a pandemic.

There is therefore currently increased interest in a strengthening and increasing the effectiveness of the body's own defence.

Active substances with an immune modulating effect are appropriate for this. The immune modulating effect can be distinguished into a so-called natural or innate immunity, which a newborn baby already has, and the adaptive or acquired immunity, which only forms in the course of life due to contact with various invaders. Adaptive immunity makes use of the T helper cells, which are an essential part of the learning capacity of the body's defence system. Of the group of T helper cells, the T helper 1 and T helper 2 cells are particularly important.

In the case of illnesses, a known and efficient treatment is to influence the so-called Th1/Th2 response such that the respective illness is combated much faster and more extensively. To this end, their effect is increased by the administration of stimulating substances.

Thus, the patent application KR 1007 42900 discloses the *Lactobacillus rhamnosus* DCC 3201 as a bacterial strain, which is added to foods as a probiotic supplement in order to counteract and prevent atopical dermatitis. Laboratory tests suggest that this bacterial strain acts to alleviate and prevent allergic reactions by maintaining the balance of T helper 1 and T helper 2 cells.

The place where this bacterial strain was found in the feces of Korean children should actually not be a disadvantage with appropriate preparation according to the prior art, however, from the start, it does not arouse exclusively positive expectations.

In any case, this bacterial strain is not expected to provide an effect if the aim is a different, targeted shifting of the T helper 1 to T helper 2 ratio, which acts on other illnesses.

Against this background, it is the object of the invention to find active substances from a group which have an immune-modulating effect in that they strengthen the immune responses of the body and in the process either reinforce the natural immunity or support the adaptive immunity by stimulating T helper cells as directly as possible to increased activity and in the process selectively and primarily direct the effect either to T helper cells 1 or to T helper cells 2.

As a solution, the invention provides a pharmaceutical and/or dietetic composition in which, for increasing the impact of the immune defence by means of T helper 1 and T helper 2 cells, bacteria of the genus *Lactobacillus fermentum* from at least one of the strains K1-Lb1 (deposition number DSM 22837) or K1-Lb6 or K2-Lb4 or K6-Lb4 or K7-Lb1 (deposition number DSM 22831) or K8-Lb1 (deposition number DSM 22832) or K9-Lb3 and/or from the genus *Lactobacillus plantarum* of the strain K4-Lb6 (deposition number DSM 22830) and/or, for strengthening the native immune response, bacteria from the genus *Lactobacillus fermentum* of at least one of the strains K2-Lb6 (deposition number DSM 22829) or K11-Lb3 (deposition number DSM 22838) are contained.

The designations KxLby used here are taken from the system used in the original investigation of Kimere. K stands for Kimere, the source of the hitherto unknown strains presented here, Lb stands for *Lactobacillus*. From the large number of investigated species, some were chosen so that the first parameter of the designation-Kx—and the second parameter of the designation-Lby—do not contain sequential numbers.

The designations Kx-Lby of the strains of the genus *Lactobacillus fermentum* lead from two alternative kinds to an unambiguous identification of the respective bacterial strain.

The first alternative is the known method of depositing a derivative of the respective genus at the DSMZ. Deutsche Samnmlung von Mikroorganisms and Zellkulturen GmbH in Inhoffenstra[beta]e 7B, D-38124 Braunschweig. According to the procedure prescribed for a patent application, intact and living examples of the bacterial strains mentioned here were deposited at the DSMZ, specifically on Aug. 6, 2009, under the following file numbers:

*Lactobacillus fermentum* K1-Lb1 (deposition number DSM 22837)

*Lactobacillus fermentum* K2-Lb6 (deposition number DSM 22829)

*Lactobacillus fermentum* K7-Lb1 (deposition number DSM 22831)

*Lactobacillus fermentum* K8-Lb1 (deposition number DSM 22832)

*Lactobacillus fermentum* K11-Lb3 (deposition number DSM 22838)

and *Lactobacillus plantarum* K4-Lb6 (deposition number DSM 22830)

The other strains have not yet been deposited at the DSMZ. For their disclosure, there serves the second alternative method of making known the PFGE band pattern.

An alternative for depositing living bacteria is clear identification by means of pulse field gel electrophoresis pattern (PFGE). In the accompanying FIG. 3, for each of the bacterial strains mentioned here, the so-called band patterns in each case, which are analysed by the PFGE method and therein show an identical band pattern, are thereby unambiguously identified as this strain of the respective genus.

The method of typifying microorganisms by PFGE has been known since 1984 and is part of the recognized prior art. The researchers Schwartz and Cantor have observed that, on application of electrical pulses, which periodically changed their orientation at a particular angle in ratio to the agarose gel, large intact DNA molecules were isolated as band pattern. This method is based on U.S. Pat. No. 4,473,452 and comprises four key steps, namely 1. Preparing the samples by culturing the microorganisms in a nutrient broth, embedding the cells in gels and obtaining immobilized, deproteinized, intact DNA molecules
2. Specifying the progress of electrophoresis for an optimum separation between the molecules
3. Loading the samples into the gels and performing pulse-field gel electrophoresis with the result of a typical band pattern
4. Analysing the band pattern by comparison with the band patterns of similar genera of microorganisms. It is generally accepted in the prior art that the band pattern thereby obtained permits a clear identification of the respective genus, somewhat comparable with a fingerprint of a person.

The PFGE process, however, is not the actual content of this patent application but only one of two methods used for unambiguous identification of the bacterial strains of the genus *Lactobacillus fermentum* to be protected. The common inventive feature of all genera is the stimulating effect on the T helper cells.

The T helper cells belong to the lymphocytes, a sub-group of the "white blood corpuscles", which are the most important agents of the human immune defence. An adult human has somewhat over a thousand different lymphatic cells, which comprise about two percent of his bodyweight. The lymphocytes, like all blood cells, originate from the bone marrow and, before their maturity into functioning cells of the immune defence, must pass through additional development and differentiation stages.

Some of these precursor cells migrate from the blood-forming tissue directly into the *thymus* gland and develop into so-called T-lymphocytes. There, they learn, inter alia, to differentiate between the body's own cells and "invaders". The remaining lymphocytes mature in the bone marrow into so-called B cells.

The most important property of the lymphocytes is their capability of reacting with a particular molecular shape according to the key-and-lock principle. To this end, as "lock" they bear on their surface receptors, which are specially adapted to the protein structure of one of millions of different foreign bodies—the "keys". Via the structure of the cell's own protein and protein that is foreign to the cell on the surface of the macrophage, they recognize a "new invader" and mount the specific immune defence.

For the actual execution of the immune defence, T killer cells are created, which selectively hind the invader and destroy it. The strengthening of this human inunune defence by active substances according to the invention takes place indirectly, namely via stimulating the increased formation of T helper cells, the B lymphocytes, to transform themselves into plasma cells, the body's antibody factories. In the course of their short lifetime of only a few days, they can pour out thousands of specialized defence molecules per second.

It is at this point that the effect of the bacterial strains presented here starts, in that they act on one of the two types of T helper cells, either increasing the number of T helper 1 or T helper 2 cells, as a result of which the number of the respective other kind is inevitably reduced, and additionally or alternatively thereto, increasing the number of T helper cells that are grown overall.

By means of an additionally growing proportion of a very particular type within the group of T helper cells, their number with respect to the normal state increases strongly, firstly due to the absolute increase and secondly due to the increase of the relative proportion of the total number of all T helper cells. As a result, a very much larger number of plasma cells for defence molecules is very rapidly formed. Thus, the number of these defence molecules with a total of three factors is increased, namely the absolute and the relative increase of the number of T helper cells and their effect strengthening by multiplication in the plasma cells.

A further, more advantageous strengthening factor for this effect is that, due to the selection of one of the genera presented here, those plasma cells that form precisely the required antibodies are predominantly formed. Due to the larger number of the bacterial strains presented here, it is possible to select that bacterial strain that forms antibodies that are particular effective for a particular type of invader. If, for example, a patient suffers from an allergy, it is appropriate to select one of the strains K1-Lb1 (deposition number DSM 22837), K2Lb4, K4-Lb6 (deposition number DSM 22830), K6-Lb4 or K9-Lb3.

In addition, the immune system is prepared for a further contact with the invader in that, the characteristic features of the invading foreign substance is stored in a portion of the B cells, so that, with the next invasion, the production of the suitable antibodies can start directly. This "secondary immune response" is the basis of most protective inoculations.

A further advantage of the large number of the bacterial kinds presented here is their multiple effect in multimorbid patients, that is to say patients that suffer from more than one single illness. If, for example, the above-mentioned allergy patient additionally suffers from hyperactivity of the gall bladder, the bacterial type K4-Lb6 (deposition number DSM 22830) is therefore of particular advantage, since it has a particularly high bile salt resistance and, despite this second problem, therefore still has the first desirable antiallergenic effect.

Another advantageous property of the bacterial strains presented here is their probiotic property. This property is proven inter alia by the fact that all strains were isolated from a food that has successfully been used for generations, namely from Kimere, a dough produced from pearl millet (*Pennisetum* claucum) by spontaneous fermentation, whose place of origin is the district of Mbeere in Kenya. Since all types of bacteria are contained in a greater or lesser concentration in this widespread and preferentially used staple food, their compatibility is proven. It is also proven thereby that, in comparison to a very large number of allopathic medicines, it can be classified as almost free of side effects.

The selection of bacilli of the genus *Lactobacillus fermentum* was induced by the investigation of the typical conditions for the traditional production of Kimere, namely the hygienic conditions during the preparation of the starting material pearl millet, its processing by water treatment in very few vessels, which by our standards have only been inadequately cleaned, its processing by grinding in a moist state usually with one and the same mill, and its fermentation generally in one and the same vessel reserved for this purpose. That would, by European standards, raise fears of contamination by microorganisms disadvantageous to humans.

However, the investigation has shown that this is very clearly not the case, but at least 90% of the microorganisms found belonged to the genus *Lactobacillus fermentum*. From this it can not only be concluded that this genus is generally compatible with humans, but that it suppresses, or for the most part eliminates, other microorganisms that are less compatible with humans.

In the studies, the population with microorganisms in the case of Kimere has generally proved very stable, which is a positive feature for the use of the kinds of bacteria found there. A further advantage is the relatively acid milieu, that is to say a relatively low pH. Since the microorganisms have proven long-term stable in this acid milieu, they will also survive the acid environment in the stomach and gut and in this manner will prove effective on oral administration—for example as food supplement.

Strains were even found that are characterised by such a high degree of acid resistance that they pass through the stomach and small intestine even into the large intestine in order to develop their healing effect there.

Of the bacterial strains recognised as effective, almost all act not only against a single type of complaint, but against a plurality thereof, so that they are also suitable inter alia for treatment of those with multiple illnesses. However, clear focuses of the type of effect were found, so that the individual bacterial types can be selectively assigned to a focal action.

The first of the discovered types of effect is a strengthening of the immune defence by a clear shifting of the T helper cells away from T helper 2 cells towards T helper 1 cells. The strains K1-Lb1 (deposition number DSM 22837), K1-Lb6, K2-Lb4, K4-Lb6 (deposition number DSM 22830), K6-Lb4 and K9-Lb3 act predominantly with this focus. FIG. 1 shows the result of the in vitro simulated effect. The different intensities of this type of effect can be read off in three stages.

These bacterial strains are thus suitable for medicines, food supplements or pharmaceutical preparations for the prophylactic treatment or reduction of the risk of the manifestation or for therapy of T helper 2-driven illnesses, such as, for example, eczema and/or atopical dermatitis and/or asthma and/or rhinitis allergica or other allergies and/or tuberculosis and/or colitis ulcers and/or eosinophilic pneumonia.

These bacterial strains are thus suitable for medicines, food supplements or pharmaceutical preparations for the prophylactic treatment or for therapy in complaints, infections or other illnesses whose defence is Th1 mediated, for example gut infections and/or travel diarrhoea and/or colds and/or urogenital infections and/or HIV-associated complications and complaints and/or candidiasis.

Of the bacterial strains found, some act with a contrary accent of the T helper cells: they effect a displacement of the response away from the T helper 1 cells towards the T helper 2 cells. Thereby, bacterial strains are presented which are also usable for entirely different illnesses in the same advantageous manner. This effect predominantly characterises the strains K6-Lb2. K7-Lb1 (deposition number DSM 22831) and K8-Lb1 (deposition number DSM 22832).

These strains which predominantly effect a reinforcement of the immune defence by shifting away from the T helper 1 and towards the T helper 2 responses, are suitable for producing a medicine or a food supplement or a pharmaceutical preparation for prophylactic treatment or for reducing the risk of manifestation of autoimmune illnesses such as Crohn's disease or other T Helper 1-driven illnesses.

The aforementioned strains K6-Lb2, K7-Lb1 (deposition number DSM 22831) and K8-Lb1 (deposition number DSM 22832) also have an inhibiting effect against inflammation. And the K6-Lb4 strain also proves anti-inflammatory. These bacterial strains are therefore suitable for producing a medicine or a food supplement or a pharmaceutical preparation for the reduction or elimination of the effects of autoimmune illnesses such as arthritis or dermatitis or allergies or illnesses with an inflammatory component, such as a metabolic syndrome or arteriosclerosis.

The aforementioned strains K6-Lb2, K7-Lb1 (deposition number DSM 22831), K8-Lb1 (deposition number DSM 22832) and K6-Lb4 can be suitably and efficiently used for the prophylaxis or therapy of rheumatoid arthritis, Hashimoto thyreoditis, uveitis, psoriasis, type 1 diabetes, Sjögren disease, coeliac disease, systemic lupus erythematosus, ankylosing spondylitis, Crohn's disease, inflammatory intestinal diseases, scleroderma, sarcoidosis, multiple sclerosis, vitiligo, Grave's autoimmune thyroiditis, endocrinous opthalmopathy, myasthenia gravis, osteoarthritis, arteriosclerosis and therefore also cardiac infarction, other peripheral arterial occlusive diseases, cerebral infarction (stroke), metabolic syndrome and therefore also in the case of adipositas, hypertonia, insulin resistance, type 2 diabetes, dyslipoproteinaemia, and amyotrophic lateral sclerosis, interstitial cystitis and/or irritable bowel syndrome (IBS).

Some of the bacterial strains presented here additionally strengthen the immune defence in that they effect an increased release of defensin from the intestinal cells. It is also known that defensins carry many cationic and hydrophobic amino acid residues. They are thus amphipathic peptides. These positive charges interact with the negative charges of the exciter membranes. The preference of the defensins is for membranes that are characterised by a low proportion of cholesterol and thereby differ from those of eukaryotic organisms. When they have penetrated the membrane, they also interact with anionic molecules within the pathogen cell, such as DNA and RNA. By this means the action spectrum is broad and corresponds to that of a broad-spectrum antibiotic, so that it is difficult for a pathogen to counteract the mechanism of the defensins.

To this extent, the effect mechanism is similar to that of the T helper cells, and they are therefore to be assigned to the same inventive idea. This type of effect applies predominantly to the strains K1-Lb7, K2-Lb6 (deposition number DSM 22829) and K11-Lb3 (deposition number DSM 22838).

A further outstanding property is tolerance to a 3% bile salt solution. This feature applies particularly to the K4-Lb6 (deposition number DSM 22830) strain. It ensures its survival through the greatest portion of the human digestive system as far as the large intestine. Because the bacterium is still in the living state when it arrives there it can still develop its healing effect, namely the strengthening of the T helper 1 reaction and the weakening of the T helper 2 influence.

For a very much larger number of the bacterial strains presented here, survival in the intestines is no longer possible, but survival in the stomach is. At least 8% of them survive a pH of 3.0 for at least 3 hours. By this means they can still develop their effectiveness in full even after penetrating the pylorus within the stomach. This applies to the strains K1-Lb1 (deposition number DSM 22837), K1-Lb6, K2-Lb4, K4-Lb6 (deposition number DSM 22830), K6-Lb2, K6-Lb4, K7-Lb1 (deposition number DSM 22831), K8-Lb1 (deposition number DSM 22832) and K9-Lb3.

These strains are therefore, inter aka, appropriate for prophylaxis for the following complaints and illnesses, to avoid passing to a chronic state and for system-related therapy of osteoporosis by acidification of the milieu and displacement of other microorganisms with the result of improved mineral and trace element resorption. Likewise, they are appropriate for liver failures and hepatic encephalopathy by reduction or inhibition of the resorption of toxins.

By means of these strains, lesser complaints with obstipation, irritable bowel syndrome and halitosis can be reached.

By means of the strains, the effects of lactose intolerance can be successfully suppressed by supporting lactose utilization and lactose digestion.

Thanks to these bacterial strains, a positive influencing of the bile acid and cholesterol metabolism can also be achieved.

In a medicine or another form of administration, they are also helpful against vaginosis or vaginitis, specific with oral or topical application.

Another type of effect is the influencing of the concentration and composition at the membrane or wall of a bacterium, and consequently for modulation of the immune response of the recipient, at least one of the strains expresses a glycosyl transferase or a sugar transferase or an acyl transferase or a lipoteichoic acid-exporting protein.

It is also observed as an effect mechanism that in the case of at least one of the strains for glycosyl transferase, the sugar residue docking can be catalysed by the diacylglycerol synthesis (DAG).

Another subvariant is that for at least one of the strains, acyl transferases can be catalysed by the diacylglycerol synthesis (DAG).

In another variant of the effect of the bacterial strains presented here, for at least one of the strains, enzymes catalyse further sugar transfer for the synthesis of microbial peptidoglycans.

For at least one of the strains, the expulsion from the cytoplasm can be mediated by means of a lipoteichonic acid synthesis and/or by means of a peptidoglycan synthesis as transporter.

At the beginning of the description, it was mentioned that the bacterial strains presented here are identified by the deposition of at least one living example with the DSMZ. Alternatively the respective band pattern of the pulse field gel electrophoresis serves as the feature to be clearly identified. For this process, it is an appropriate intermediate step to examine whether the effect-mediating genes have a strain-specific pattern of the suppressive subtractive hybridization (SSH).

Methods and Special Features of the Underlying Study

1. Derivation from Kimere

Kimere is a spontaneously fermented dough or porridge from pearl millet, which is produced and consumed, inter alia in the district of Mbeere in Kenya. East Africa, by a traditional method by first dry, then wet, milling on a millstone and subsequent fermentation.

A special feature is that Kimere is fermented 18-24 hours before consumption and is assimilated in its actively fermented state as food or is kept for up to three days. Otherwise it is similar to the preparation of the normal East African porridge, called Uji. Kimere only differs from Uji in its viscosity and consistency, since Kimere is more viscous.

The differences result from the manufacturing method, which influences the microbial population of the final product. The production of Uji includes the mechanical milling of maize, sorghum, millet or other cereal with a hammer mill, followed by mixing the resulting meal with water and spontaneous fermentation or pouring back some of the already ready prepared Uji portion. Finally, the fermented product is boiled and sweetened before consumption.

In contrast thereto, Kimere is milled on a millstone in a dry state, followed usually by three wet milling operations with decanting and finally a fermentation. In a variant, a portion of the product is converted to a thin slime, to which water is added and then boiled. The boiled Kimere is then mixed with the unboiled again.

The biggest difference from Uji is that Kimere is consumed in its actively fermenting stage, and therefore contains living microorganisms, by contrast Uji is consumed immediately after boiling and does not therefore contain living fermenting microorganisms. This method of manufacturing Kimere is typical of the regions of Mbeere, Tharaka, Chuk and Embu east of Mount Kenya.

After the first purification process and the dry grinding, the broken grain easily absorbs water—about 30% by volume—and is soaked for about 30 to 60 minutes at room temperature. As a result, the broken grains are softened and prepared for the following wet grinding processes.

This is followed by a total of three wet grinding processes with a thick porridge as result. Between each wet grinding process, further water is added and after each milling operation, decanting is performed. The result is a milky suspension, of which two thirds is boiled with stirring.

After boiling it is charged together with the further unboiled third into a fermentation vessel and left to ferment for 18 to 24 hours. The unbolted portion contains the microbes that were contained in the grains and which have been absorbed during the milling operations.

Usually a portion of a previous preparation of Kimere is added, which speeds up the fermentation and influences the ultimate microbial population. During fermentation, as a result of the lactobacilli, the proportion of phythates is reduced; pathogens are reduced and the flavour is improved.

The nutritional value of Kimere was thus improved compared to non-fermented products and is free of *coli* bacteria and other enterobacteria, which is an indication of microbial safety. The presence of living bacteria in Kimere is of particular interest, since it is the basis of a probiotic application.

2. Intake and Preparation of the Kimere Samples

The samples were taken in 11 yards in Kathera, a part of Kiang'Ombe, the Evurore part of the district of Mbeere. The samples were prepared and placed overnight in fermentation vessels. On the following morning, they were collected and taken to the Max-Rubner Institute in Kiel in a screw top glass jar, where they were stored for a maximum of 24 hours at 4[deg.] Celsius.

Transportation took less than eight hours, during which the samples were conveyed at normal room temperature.

By this means, it was ensured that the isolated microorganisms behaved in a similar way to the microbial population during the otherwise conventional fermentation, since Kimere is fermented for 18 to 24 hours before consumption and can be consumed from the same fermentation vessel for another three days thereafter.

The samples were very well mixed in a vortex mixer. 1 g of the sample was added to 9 ml of sterile Ringer's solution to obtain a dilution of 10<−1>. Then series of dilutions were made down to 10<−8> to count the lactobacilli.

3. Determining the pH of Kimere

To determine the pH of Kimere samples, the method of the AOAC (Association of Analytical Communities) in the version of 1995 was applied. 10 g of the samples in each case was mixed with 40 ml of double-distilled water; the mixture was measured after a waiting time of 10 minutes using a Delta 320 pH measuring instrument. The pH values were measured in triplicate and the average value was calculated.

The aerobic mesophiles were counted on a plate count agar (PCA) and aerobically incubated at 30[deg.] C. for 48 hours. The number of lactobacilli was determined by the area counting method on an MRS agar (Merck, Darmstadt, Germany) according to the process of De Man et. al. of 1960, and on the M17 agar (Merck, Darmstadt. Germany).

The MRS agar plates were incubated in an anaerobic chamber (MACS MG500+TG Airlock, dw-scientific, Shipley, West Yorkshire, England) at 37[deg.] C. for 48 hours. The gas atmosphere consisted of 10% hydrogen, 10% carbon dioxide and 80% nitrogen.

Then the M17 agar plates were aerobically incubated at 30[deg.] C. for 48 hours. Only plates with colony-forming units (cfu) between 10 and 300 per gram were analysed and the result was plotted as a decadic logarithm of the cfu number per gram of the wet weight of the sample.

4. Isolation and Biochemical Characterization of the Lactobacilli 1 g of the sample of Kimere was weighed in 9 ml Ringer's solution and a plurality of tenfold dilutions were prepared down to 10<−8>. Of each dilution of 10<−5> to 10<−8>. 0.1 ml in each case was spread two fold on an MRS agar plate. The plates were incubated at 37[deg.] C. for 48 hours in an aerobic chamber as described above.

Individual, different colonies were chosen based on their morphology and purified by spreading again on MRS agar, and inspected with the microscope. The gram staining and the catalase reaction were performed as described by Harrigan and McCance 1990.

All rod-shaped gram-positive and catalase-negative isolates were stored at −80[deg.] C. in the Cryo-Bank® vials from Germany for further characterizations. The production of CO2 glucose in MRS solution was determined by means of Durham tubes. The chemical characterisation of the chains was performed with API 50 CH kits with API 50 CHL medium in conformity with the guidelines of the manufacturer Biomérieux. Nürtingen, Germany, and by the fermentation of various carbohydrates in MRS solution. The isolates were also tested for their capability for growth at 15[deg.] C. and 45[deg.] C.

5. Molecular Characterisation of the Lactobacilli by Means of the Amplified Ribosomal DNA Restriction Analysis (ARDRA)

The DNA material for the polymerase chain reaction (PCR) was prepared according to the method of Ismail 2007 and Vaneechoutte et. al. 1992: A colony from an MRS agar plate was dissolved in 500 [mu]l of PCR buffer solution to produce a turbid suspension (McFarland 3) and incubated in a Thermomixer at 95[deg.] C. for ten minutes. This DNA material was stored at −20[deg.] C. until the PCA analysis was performed.

The PCR was performed in an Eppendorf Mastercycler 5330, Hamburg. Germany, in volume units of 50 [mu]l, consisting of 20 [mu]l PCR master mixture (Fermentas, Sankt Leon-Roth, Germany). 26 [mu]l double-distilled water, 1 [mu]l of the respective primer and 2 [mu]l of the DNA sample. The PCR program was Initial denaturisation at 93[deg.] C. for five minutes, 35 cycles of denaturisation at 92[deg.]C. for one minute, hardening at 58[deg.] C. for 1.5 minutes and elongation at 72[deg.] C. for 2.5 minutes respectively, followed by a final elongation at 72[deg.] C. for ten minutes and cooling and keeping at 4[deg.] C.

These sequences of oligonucleotide primers were: forward-UP68 5'-TGG CTC AGA TTG AAC GC GGC GGC-3' and reverse-UP69 5'-CCT TTC CCT CAC GGT ACT GGT-3'. An amplification of about 2.4 kb was produced, which for the most part consisted of the 16S rDNA. 16S-23SrDNA spacer region and portions of the 23SrDNA-stand (Ismail, 2007, Vaneechoutte et al 1992). The restriction was performed overnight at suitable temperatures in 20 [mu]l volume units, which contained 0.5 [mu]l restriction enzyme (HaelII., Hinfl.) (Fermentas) DdeI (New England Bio Labs Inc.), 2 [mu]l enzyme buffer solution (Buffers R for HaelII. and Hinfl and Buffer 3 for DdeI), 2.5 [mu]l-15.5 Ml 1*TE buffer, and 2.5-15 [mu]l PCR product.

The used volume was based on the strength of the signal from the PCR products, which were analysed on the pattern of the agarose gel restriction fragment by electrophoresis in 1.5% agarose gel in 1*TAE buffer at 80 V for two hours. Staining was performed with ethidium bromide for 30 minutes, followed by washing for 15 minutes in water. The photographs were taken under UV light.

6. Strain-Specific PCR for *Lactobacillus fermentum*

Strain-specific PCR was performed according to the method described by Dickson et. al. 2005. Primary LF1 (nt196-215; 5'-AAT ACC GCA TTA CAA CTT TG-3) and LF2 (nt529-510; 5'-GGT TAA ATA CCG TCA ACG TA-3') were used specifically for *Lactobacillus fermentum*. An amplification of 337 bp length was proxtuced. The amplification program was used without change. The PCR products were analysed as described for ARDRA.

7. 16S rDNA Sequences:

Based on the ARDRA profile data in each case (chart 2-2). 12 strains were chosen for sequencing. The strains were chosen based on the profiles that had been chosen after application of the Hinfl restriction enzyme. Five strains that represented each of the two ARDRA profiles (A1 and A2) and one of the profiles B and C in each case. The PCR products generated with the primers UP68 (forwards) and UP 69 (backwards) (Vaneechoutte et. al. 1992), were purified with a clean up kit (NucleoSpin® Extract II. Macherey-Nagel. Dtiren, Germany) according to the manufacturer's operating instructions. Purification was controlled by electrophoresis in 1% agarose gel. Partial sequencing of 16S rDNA was performed using UP68 as sequencing primer. Sequencing was performed at MWG Biotech AG in Ebersberg, Germany.

8. Pulse Field Gel Electrophoresis (PFGE)

PFGE analysis of *lactobacillus fermentum* strains was performed according to the method of Hoppe-Seyler et al. 2003. The restriction enzymes that were tested were NotI, AscI and SmaI. AscI gave the best profiles and was used in this study. Electrophoresis was performed in a Bio-Rad CHEF-DRII system which was adjusted to the following conditions: Temperature 14[deg.] C., pump rate 70 rpm, first switching time 2.0 seconds, final switching time 30 seconds, running time 24 hours and voltage 175 volt. After electrophoresis, the gel was soaked in ethidium bromide (0.5 mg/l) for 30 minutes. The gel was then washed in distilled water for 10 minutes and photographed under UV light.

9. Data Analysis

The microbiological quality of the colony-forming units (cfu) and the pH were analyzed using SAS version 9.1. The ARDRA gels were visually analysed and the patterns compared with those of typical strains and brought to agreement. The orientation of the 16S rDNA sequences and the generation of the dendogram were based on *Escherichia coli* ATCC11775T (access number X80725) as a root of the dendrogram (Tamura et. al. 2007) with the MEGA4 neighbour-joining method.

The sequences were also compared with the sequences in the gene bank for the DNA data using the BLAST algorithm (Altschul et. al. 1997). The PGGE profiles were analysed using the GelCompar II program (Applied Maths, Kortrijk, Belgium). Similarities between different chains were derived using Dice's coefficient. The unweighted pair group method with arithmetic mean (UPGMA) was used to cluster different profiles.

10. Microbiological Quality of Kimere

Lactobacilli make up the biggest portion of the microbial population of fermented Kimere. *Coli* bacteria and other enterobacteria were detected neither in 0.1 gram of the sample in testing in LST nor in 0.01 gram of the sample on VRB agar, nor in 0.01 grain of the sample on VRBD.

11. Biochemical Characterization of the Lactobacilli 48 strains of isolated lactobacilli were examined for growth at growth at 15[deg.] C. and at 45[deg.] C. and for their gas production from glucose and for the capability to metabolize various sugars. In addition, they were characterized by API 50CHL. All strains with the exception of K1-Lb5 were capable of growing on melibiose and raffinose. All strains with the exception of the isolated K4-Lb6 (deposition number DSM 22830) were capable of growing on mannitol, melecitose, rhamnose, sorbitol and trehalose. Only three isolates were capable of growing on cellobiose. Most strains with the exception of K4-Lb6 (deposition number DSM 22830) were capable of growing at 45[deg.] C.

By the identification according to API 50CHL, 33 strains of *Lactobacillus fermentum* could be isolated. The API identity points extended from 38.9 to 99.9%.

12. PFGE Profiles of the Kimere Isolates

All isolates from Kimere, which was identified as *Lactobacillus fermentum*, were subjected to PFGE analysis. Of the restriction enzymes that were used for testing (AscI, NotI, SmaI), only AscI produced results suitable for comparison. FIG. 3 shows the profiles of the 10 strains disclosed here. Although they have only been isolated from a single kind of fermented food, most kinds show fairly different PFGE patterns, which illustrates the high biodiversification within the strains of *Lactobacillus fermentum* from Kimere.

The very significant differences of the band patterns between the individual strains also make it plausible that a clear identification is possible using this band pattern.

12. Strain-Specific Immunomodulation of the Strains of *Lactobacillus fermentum* Isolated from Kimere It indicates that probiotic effects are strain-specific. So far, very few studies have compared strains of the same genus to reach this conclusion. With the study described here, the probiotic potential of strains of the genus *Lactobacillus fermentum* are investigated and demonstrated strain-specifically in vitro. Nine strains of *Lactobacillus fermentum* and one strain of *Lactobacillus plantarum*, which could grow in a 3% bile salt solution, were selected from 48 strains by a bile tolerance test.

These strains were further investigated, namely for their growth rate in an MRS medium (Man Rogosa and Sharpe), supplemented with 0.3% and 3% bile salt solution and for their resistance to a low-pHl by counting the surviving colony-forming units (cfu) after exposure to pH 2 and pH 3 for three hours.

The immune-modulating potential was investigated by co-incubation of the strains with human peripheral blood mononuclear cells (PBMCs) for 48 hours at 3TC and measurement of the cytokines, specifically for Th 1 cytokines (interferon-[gamma]) and Th2 cytokines (Interleukin-4) in the supernatants by enzymatic-linked immunosorbent assay (ELISA).

All strains could tolerate 0.3 bile acid, with strain K4-Lb6 (deposition number DSM 22830) even withstanding 3.0% bile acid. The K7-Lb1 (deposition number DSM 22831) and K8-Lb1 (deposition number DSM 22832) strains even showed a survival rate of about 53% and 27.2% at a pH of 2.0; by contrast most strains only remained intact at a pH of 3.0.

As with LGG, the strains K7-Lb1 (deposition number DSM 22831) and K8-Lb1 (deposition number DSM 22832) reduced interleukin-4. LGG and all other strains induced a changed from the basal Th1/Th2 ratio towards Th1 with the exception of the strains K7-Lb1 (deposition number DSM 22831) and K8-Lb1 (deposition number DSM 22832) induced a change towards Th2. The SEA-stimulated Th1/Th2 ratio was reduced from the *Lactobacillus fermentum* strains, while, by contrast, it was raised by LGG.

The study thus shows strain-specific peculiarities of the strains of *Lactobacillus fermentum* and also shows the capability of suppressing the production of interferon-[gamma] induced by *Staphylococcus* entertoxin A (SEA), a property that has not been reported by earlier studies of *Lactobacillus fermentum* and of most other Lactobacilli. These various properties can be used to combat illnesses that are driven by a Th response or a Th2 response.

13. Fermented Probiotic Food Supplements and their Effect on the Immune System

The application of lactic acid bacteria (LAB) for human nutrition has been known for millennia-wherever fermented milk or other fermented foods have been enjoyed. Their direct association with human health was first observed in 1908 by the Russian Nobel laureate Elie Metchnikoff, who ascribed the health and longevity of Bulgarian herdsmen to the microorganisms in the yoghurt that they frequently consumed.

The observations found new interest when the use of Lactobacilli and Bifidobacteria gained importance as food supplements. "Probiotic" is defined as "A live microbial feed supplement which beneficially affects the host animal by improving its intestinal microbial balance." (Füller. R. 1989. Probiotics in Man and Animals. Journal of Applied Bacteriology 66, 365-378).

The definition and application of "probiotics" continued to develop as soon as scientific evidence had been obtained (Schrezenmeir. J. and de Vrese, M., 2001, Probiotics, Pre-biotics and Synbiotics, approaching a definition. American Journal of Clinical Nutrition 73, 361-364.) A more recent proposal by Galdiano. C. M., de LeBlanc, A. D., Vinderola, G., Bonet, A. E. B, and Perdigon, G., 2007, Proposed Model: Mechanisms of immunomodulation induced by probiotic bacteria. Clinical and Vaccine Immunology 14, 485-492) includes immunomodulation in the definition of probiotics. They defined probiotic as "living microorganisms that, when added to foods, influence the composition and activity of the microbes in the digestive system, modulate the inflammatory reaction, improve the non-specific barriers in the gut and strengthen or improve the immune response of the mucosae and of the system."

The selection of strains for use as probiotics concentrates on two key properties: The adaptability of the strain itself and the health-supporting or functional aspect. These selection schemes include: Survival in a milieu with low pH, growth in the presence of bile salts, adhesion to epithelial cells on the intestinal wall, colonization within the digestion system, maintaining the microbial equilibrium, non-pathogenicity towards the recipient, resistance to technical stress during processing and distribution and, finally, the capability to improve the health of the recipient. (FAO/WHO, 2002, Guidelines for the evaluation of Probiotics in food. Joint FAO/WHO Working group report on Drafting Guidelines for the evaluation of Probiotics in food ftp://ftp.fao.org/es/esn/food/wgre-port2.pdf, 1-1).

It must be noted here that not every individual probiotic strain must show all these properties. According to recent scientific findings, bacteria must not be "living" to product immunomodulating effects since both living and dead bacteria or only bacterial DNA demonstrably shows some health benefits.

However, survival in the digestion system is essential to ensure that the probiotics reach the target in the active state, depending on the functional requirements such as colonization of the digestion system and the exclusion of putrefactive bacteria or pathogens.

Immunomodulation by probiotics is achieved by interaction with the immune cells of the recipient and the secretion of various signal molecules, such as cytokines and immunoglobulins. The T helper cells perform an outstanding role within the immunocompetent cells in the immunomodulation, which produces cytokines by means of probiotics.

In interaction with the antigens, available T helper cells differ in various ways, depending on the type and number of the antigens. The environment of the cytokines ultimately determines the family relationship and the effect profile. The differentiation into T helper 1 cells depends on the interleukin 12-effected activation of transcription 4 (STAT4), which leads to interferon-[gamma] production, which, via a series of cascades, leads to a further growth of T-bet-guided transcription factors, which leads to a further growth of interferon-[gamma], interleukin-12 receptors [beta]2, interleukin-4 suppression and the maintenance of family relationships to T helper 1 cells.

On the other hand, T helper 2 cells differ in the presence of interleukin-4 by STATE, an increase of interleukin-4 production, the suppression of interferon-[gamma] production and thus maintenance of T helper 2 descent.

The other kind of differentiation of T helper cells is T regulation (Treg), which produces interleukin 10. Treg cytokines IL-10 regulate the immune system both due to the suppression of T helper 1 cells as well as of T helper 2 cytokines by ensuring peripheral tolerances. The fourth known kind of natural T helper cells is differentiation via interleukin 23, which leads to the production of interleukin 17.

It is assumed that a disequilibrium between T helper 1, T helper 2, Treg and T17 cells is the precursor to a manifestation of various pathological conditions. The probiotic function increases cytokine production towards a reinforcement of the immune defence, a reduced allergic or autoimmune reaction and/or a lower inflammation reaction.

A modulation of cytokine production by probiotics in human and animal models was found both in vitro (Pochard, E., Gosset, P., Grangette. C, Andre, C, Tonnel, A. B., Pestel, J., Mercenier, A., 2002, Lactic acid bacteria inhibit T(H)2-cytokine-production by mononuclear cells from allergic patients. Journal of Allergy and Clinical Immunology 110, 617-623, and Ghadimi, D., Folster-Holst. R., de Vrese, M., Winkler, P., Hleller, K. J., Schrezenmeir, J., 2008. Effects of probiotic bacteria and their genomic DNA on TH1/TH2 cytokines production by peripheral blood mononuclear cells (pbmcs) of healthy and allergic subjects, Immunobiology 213, 677-692) and in vivo (Kopp, M. V., Goldstein, M., Dietschek, A., Sofke, J., Heinzmann, A. and Urbanek, R., 2008. *Lactobacillus* GG has in vitro effects on enhanced Interleukin-10 and Interferon-[gamma]-release of mononuclear cells but no in vivo effects in supplemented mothers and their neonates). Clinical and Experimental Allergy 38, 602-610).

In most cases, a mixture of Th1, Treg and Th2 cytokines was detected, although several authors include an exchange of Th1 or Th2 in the action sequence. This immunomodulation depends on the dose and time and also shows dependencies on the inoculation of the strains.

14. Bacterial Cultures

The bacterial strains used in this study are isolated from Kimere, a fermented dough from Kenya and characterised according to molecular methods and kept at −80[deg.] Celsius in a MAST Cryobank® (MAST Diagnostic, Reinfeld, Germany). As positive comparison controls for T helper 1 cytokines and T helper 2 cytokines, the strains *Lactobacillus rhamnosus* GG (ATCC 5310, a strain that is known to stimulate interferon-[gamma]) and *Escherichia coli* TG1 (BU-00035, a strain that is known to stimulate interleukin-4). They were procured from commercial sources.

The Lactobacilli were cultured anaerobically overnight in MRS solution at 3TC in an MAC8-VA500 workstation (Don Whitley Scientific Limited, UK). The *Escherichia coli* TG1 were cultured aerobically overnight at 37[deg.] in a Luria-Bertani (LB) solution. The cells were centrifuged for two minutes at 14,000 g (corresponding to 144.500 rpm on an Eppendorf Minispin Plus centrifuge). The bacterial pellets were washed twice with a phosphate-buffered salt solution (PBS) dissolved in 1 ml PBS, containing 20% glycerine, then counted in an improved Neubauer type hemocytometer and subsequently brought to a concentration of 10<8> cells per millilitre in a PBS solution with 20% glycerine and kept at −80[deg.] Celsius until use.

15. Resistance to Bile Salts 48 isolates of Lactobacilli were tested for their resistance to bile salts according to the above-described method with small changes. 0.1 ml of an MRS growth culture was added to 9.9 ml of MRS solution with 0.3 or 0.5 or 1.0 or 2.0 or 3% cattle bile (Siegmar). They were incubated for 24 hours at 37[deg.] Celsius. The growth was recorded after visual checking of the turbidity of the tubes.

Ten isolates were selected, which even showed growth with 3% ox bile. Their growth was then monitored with 0.3% and 3% ox bile. 2 ml as aliquot (partial sample) of Lactobacilli from a fresh culture grown overnight was suspended in PBS as spheres and 100 [mu]l thereof was inoculated into an MRS solution, to which 0.3% (w/v) bile solution had been added. A 0.3% (w/v) bile salt concentration has been classified as physiologically relevant and in many studies serves for probiotic selection. The same applies to a 3% ox bile (w/w).

The cultures were incubated in the water bath at 37[deg.] Celsius. The growth was observed hourly by measurement of the absorption at 620 nm (A Index 620 nm). The tests were repeated 3 times. The absorption values were recorded over the incubation times as described by Gilliand and Walker. (Gilliand, S. E. and Walker, D K 1990. Factors to consider when selecting a culture of *Lactobacillus acidophi-* lus as a dietary adjunct to produce a hypocholesterolemic effect in humans, Journal of Dairy Science 73.905-911).

16. Acid Resistance 2 ml of a culture grown overnight was centrifuged for one minute at 14,000 g (corresponding to 145,400 rpm on an Eppendorf Minispin Plus centrifuge). The pellets were washed twice with 2 ml Ringer's solution and suspended again in 1.5 ml Ringer's solution. 0.1 ml of the suspension was transferred to 5 ml of 0.35% NaCl solution (supplemented with pepsin (0.1 gram per 50 ml) and adjusted to the various pH values 2.0 and 3.0 and 6.5 with HCl), followed by incubation at 37[deg.] Celsius in a water bath.

After three hours, 5 ml of 0.1 M phosphate buffer solution with a pH of 6.5 was added. The survival rates were detected by counting on MRS agar. The colony-forming units (cfu) were expressed as a percentage of the control values that had been obtained on incubation with a pH of 6.5.

17. Test of Immunomodulation with PBMCs (Peripheral Blood Mononuclear Cells).

Complete blood was collected from healthy donors aged between 21 and 52 years and mixed with EDTA (ethylenediaminetetraacetic acid) for purposes of anticoagulation. Individuals who had reported an allergy or had recently suffered infections of the respiratory passages or had taken medication were excluded. The enlisting of test subjects and taking of blood samples was performed according to strict ethical points of view which had been laid down by the ethics committee of the University of Kiel for the use of human test subjects in research. A written agreement was obtained from all test persons before their registration for this study. The samples were kept at room temperature (18-25[deg.] Celsius) until isolation of the PBMCs.

The PBMCs were isolated as described above. Blood was mixed with sodium chloride (NaCl) and filled into 50 ml centrifuge tubes at a mixing ratio of 1:1 and placed on a Ficoll Lymphoprep Plus (Axis Shield PoC AS, Oslo, Norway) at a ratio of 1:2 (16 ml Ficoll and 32 ml blood) after centrifuging at 179.5 g (1,300 rpm) on an Eppendorf centrifuge 5810 R, r=9.5 cm) for 30 minutes at 18[deg.] C. The PBMC layers were filled into sterile centrifuge tubes with 50 ml content. Washing liquor (PBS plus 10% FCS) was added to fill the tubes (about 25 ml) and then to centrifuge them at 179.5 g for 10 minutes at 4[deg.] Celsius.

Washing was performed three times with PBS plus 10% FCS; each time, half of the washing medium was discarded of and finally the entire washing medium was removed. After the third washing, the PBMCs were suspended in the complete medium (RPMI 1640 Medium+10% FCS+1% (penicillin+streptomycin)) all supplied by Gibco, Karlsruhe. Germany. The PBMCs were counted in a hemocytometer. 10 [mu]l:90 [mu]l, PBMCs:staining agent and expressed as PBMCs/ml of the medium.

18. Coincubators of the PBMCs and Bacteria:

The concentration of PBMCs that was used was $1*10^8$ lines/ml and the bacteria $2*10^7$ cells/ml (1:20 PBMC to bacteria ratio). Besides the underlying condition (medium), with the use of *Staphylococcus* entertoxin A (SEA), a stimulating state was measured at a concentration of 2 [mu]g/ml. The treatments were: PBMC's+medium as comparison parameter; PBMC's+SEA+medium; PBMC's+bacteria+medium and PBMC's+SEA+bacteria+medium, in each case in 1 ml volume units in a plate with 24 wells and in duplicate. After incubation at 37[deg.] C. for 48 hours, the supernatant was centrifuged at 179.5 g, 4[deg.] Celsius for ten minutes and then filtered through a sterile microfilter with 0.2 [mu]m mesh size, and filled into Eppendorf tubes (1.5 ml) in volume units of 250 [mu]l and kept at -20[deg.] C. for the ELISA test.

19. Cytokine Sample

Examination of the detection of interleukin and interferon-[gamma] in the supernatants was performed with an ELISA plate with 96 wells, corresponding to the manufacturer's directions. All ELISA reagents were purchased from Mabtech AG, Hamburg. Germany. The lower detection limits were 1 pg/ml for interleukin and 4.2 pg/ml for interferon-[gamma], as recommended for each kit.

The absorption was measured at 450 and 570 nm wavelength in a microplate reader, Molecular Devices, Munich. Germany. For correction of the wavelength, the reading of the optical density at 570 nm was subtracted from the value read for 450 nm. The mean absorption values of the empty plate (background control) was deducted from the standard values for the standard test specimens and the values of the samples, and then a standard curve was generated using the curve fitting program with four parameters and the derivation of the cytokine concentration in the samples.

20. Statistics

By means of ANOVA, the mean values of the bile resistance of various strains were compared. For the data for immunomodulation, the analysis was performed in two steps: First, all the strains and the comparative test samples were compared with one another. In the second step, the values of the control parameters LGG and TG1 were excluded, which are classified as "blips" for interferon-[gamma] and interleukin-4.

With the general linear model of the SPSS 9.0 simulation software, the mean values of the SEMs were derived and the mean values of different strains were compared using the "Mann-Whitney U test". With Sigma Plot 11.0, the results were presented graphically. Statistical significance was considered at $P>0.05$. To define the direction of the displacement of the ratio of T helper 1 to T helper 2 values in the immune response, the ratio of interferon-[gamma] to interleukin-4 was used. The mean ratio was defined at 100% and the values for the other test specimens were expressed as a percentage of this comparison value. Values over 100% were classified as a T helper 1 shift and values smaller than 100% as a T helper 2 shift.

21. Resistance to Bile Salts and Low pH

To check their bile tolerance, all 48 isolates were administered to an MRS medium overnight, which was adjusted to 0.3%. 0.5%. 1%, 2% and then to a proportion of 3% ox bile (w/v). By checking the average turbidity, the growth of, first, 48, then 28, 26, 21 and 12 isolates was ascertained (see FIG. 4A).

The monitoring of their growth movement (change in OD620 nm) in MRS solution, supplemented with 0.3% ox bile (w/v) shows a good growth of all strains, which was indicated by a short delay phase (FIG. 4B). Only the strains K1-Lb6 and K8-Lb1 (deposition number DSM 22832) required over three hours to reach 0.3 units of A620 nm. As shown in FIG. 4C, the growth of the strain K4-Lb6 (deposition number DSM 22830) differed significantly from the mean value of the others in a solution with 3% ox bile (w/v). The strain K4-Lb6 (deposition number DSM 22830) began to grow almost without a delay phase. For all the other strains, the growth was only visible after a prolonged incubation overnight.

If the strains were subject to a pH of 2 and a pH of 3 for three hours, they showed the different stages of survival as shown in FIG. 5. At a pH of 3, four strains, namely K1-Lb6. K7-Lb1 (deposition number DSM 22831), K8-Lb1 (deposition number DSM 22832) and K9-Lb3, showed survival rates of over 80%. Two of these, namely the K7-Lb1 (deposition number DSM 22831) and K8-Lb1 (deposition number DSM 22832) strains, showed the greatest stress resistance towards most acids with survival rates of 52.9% at pH 2.0 and 27.2% at pH of 6.5, compared to the control strains.

22. Cytokine Production Pattern

The Kimere strains supressed the SEA-induced interferon-[ganuna] production, a phenomenon that has so far not been observed for strains of Lactobacillus fermentum. The Kimere strains supressed interleukin-4 production. In the case of the strains K7-Lb1 (deposition number DSM 22831) and K8-Lb1 (deposition number DSM 22832), the interleukin-4 was reduced to close to the limit of detectability (FIG. 6B).

A strain-dependent shift of the interferon-[gamma] to interleukin-4 ratio, and therefore of the accordingly proportional ratio of T helper 1 to T helper 2, was observed (FIG. 6C).

The strains K7-Lb1 (deposition number DSM 22831) and K8-Lb1 (deposition number DSM 22832) displaced the T helper 1 to T helper 2 balance towards T helper 2, while the others induced a change towards T helper 1. All the tested strains were, in comparison to TG1-which is known to suppress interleukin-4 production-capable of significantly suppressing the production of interleukin-4. Compared to the control substances, the strains K6-Lb4 and K8-Lb1 (deposition number DSM 22832) suppressed the basal secretion of interleukin-4 (FIG. 6B).

K7-Lb1 (deposition number DSM 22831) and K8-Lb1 (deposition number DSM 22832) suppressed the SEA-induced interleukin secretion (FIG. 6B). Interleukin-4 extended from 1.96 pg/ml for K8-Lb1 (deposition number DSM 22832) (almost not detectable) to 45 pg/ml for K1-Lb1 (deposition number DSM 22837) (FIG. 6B).

The basal interferon-[gamma] production was significantly suppressed by the strains K7-Lb1 (deposition number DSM 22831) and K8-Lb (deposition number DSM 22832) (FIG. 6A).

A suppression of SEA-induced interferon-[gamma] production by the tested bacterial strains could be observed. It was particularly pronounced for the strains K7-Lb1 (deposition number DSM 22831) and K8-Lb1 (deposition number DSM 22832), but also for all other Kimere strains (FIGS. 6A to 6C).

Since the overproduction of interferon-[gamma] plays a leading role in the pathenogenesis of IBD, the reduction of interferon-[gamma] by the strains of Lactobacillus fermentum from Kimere presented here shows that these strains have an immunomodulating property, which can be used in the battle against illnesses that are dependent on T helper 1 cells. Various strains of Lactobacillus fermentum from Kimere induced either a T helper 1- or a T helper 2-driven response, depending on the respective immunomodulation.

The various strains have different stimulation effects on interferon-[gamma] and interleukin-4 (FIG. 6). The strains' ability to suppress the basal interleukin-4 formation shows their possible application for T helper 2-driven illnesses.

The ability of Lactobacillus fermentum isolates from Kimere to suppress the formation of SEA-induced interferon-[gamma] and simultaneously to block the production of interleukin-4 shows unique possibility in the suppression of autoimmune illnesses and atopic illnesses with inflammatory components.

Further details and features of the invention are explained below in greater detail with reference to graphical descriptions. However, they are not intended to limit the invention but only explain it. In schematic, view:

FIG. 1 shows an overview of the properties of the individual strains

FIG. 2 phylogenetic tree of the Lactobacilli presented here in comparison with known bacteria FIG. 3 band pattern of all 10 strains according to the PFGE process FIGS. 4A-4C tolerance of the strains to bile salt FIG. 4A: shows the number of the surviving strains on exposure to different concentrations of cattle bile.

FIG. 4B: shows the measurement of the absorption of different strains at 620 nm in 0.3% concentration of cattle bile solution.

FIG. 4C: shows the measurement of the absorption of different strains at 620 nm in 3.0% concentration of cattle bile solution.

FIG. 5 resistance of the strains to very acid milieu

FIGS. 6A-6C Th1 and Th2 cytokine production of human blood cells (PBMCs) after coincubation with the strains FIG. 6A: shows the production of interferon-γ in different strains.

FIG. 6B: shows the production of interleukin-4 in different strains.

FIG. 6C: shows the resulting ratio of interferon-γ and interleukin-4.

FIG. 1 shows, as a key property of the strains presented here, characteristic effects and their intensities. It is clear that almost all strains, with the exception of K11-Lb3 (deposition number DSM 22838), show three characteristic properties that distinguish them from one another. All of these strains have a more or less high bile salt tolerance and a greater or lesser pH tolerance. All the strains have an immunomodulating effect. This immunomodulating effect belongs either to the natural or innate immunity, such as the elevated defensin release due to the strains, in this case K2-Lb6 (deposition number DSM 22829) and K11-Lb3 (deposition number DSM 22838), or is part of the adaptive or acquired immunity, such as the influencing of the Th1/Th2 response.

FIG. 1 shows that, of the strains presented here, K1-Lb1 (deposition number DSM 22837), K1-Lb6, K2-Lb4 and K4-Lb6 (deposition number DSM 22830), strengthen the Th helper reaction and reduce the Th2 influence. The strains K2-Lb6 (deposition number DSM 22829). K6-Lb4. K7-Lb1 (deposition number DSM 22831) and K8-Lb1 (deposition number DSM 22832), on the other hand, strengthen the Th2 response and reduce the Th1 influence.

The intensity is shown in three stages. The highest of the observed values in each case is designated. Correspondingly, ++ indicates approximately [⅔] and + corresponds to about [⅓].

In FIG. 2, some of the found strains are entered in a phylogenetic tree, in which some other, adequately well know bacterial strains have been entered. This phylogenetic tree is based on partial sequences of the 16S rDNA of selected examples of ARDRA-PCR grouping of isolates of the Lactobacilli from Kimere compared with the BLAST database. The evolutionary distances were derived using the UPMGA method, the bootstrap loader program being based on 500 repetitions. To calculate the evolutionary distances, the method of maximum combined probability was used. This phylogenetic analysis was performed in MEGA4 according to Tamura et. al. 2007.

FIG. 3 shows the band patterns of all 10 strains presented here obtained by the PFGE process-pulse field gel electrophoresis. From FIG. 3, it immediately becomes clear that the individual band patterns differ from one another significantly. All the bacteria that are analysed by the PFGE method, and which show precisely this band pattern, are thereby clearly identified as this strain of the respective genus.

The method of typifying microorganisms by PFGE has been known since 1984 and is part of the recognized prior art. With the extremely low effort of depositing a single image, it permits the unambiguous identification of the respective bacterial strain.

FIG. 4A shows the number of the surviving strains on exposure to cattle bile with increasing concentration of 0.3%, via 0.5%. 1% and 2%, up to 3% cattle bile concentration (w/v).

Figure 2:
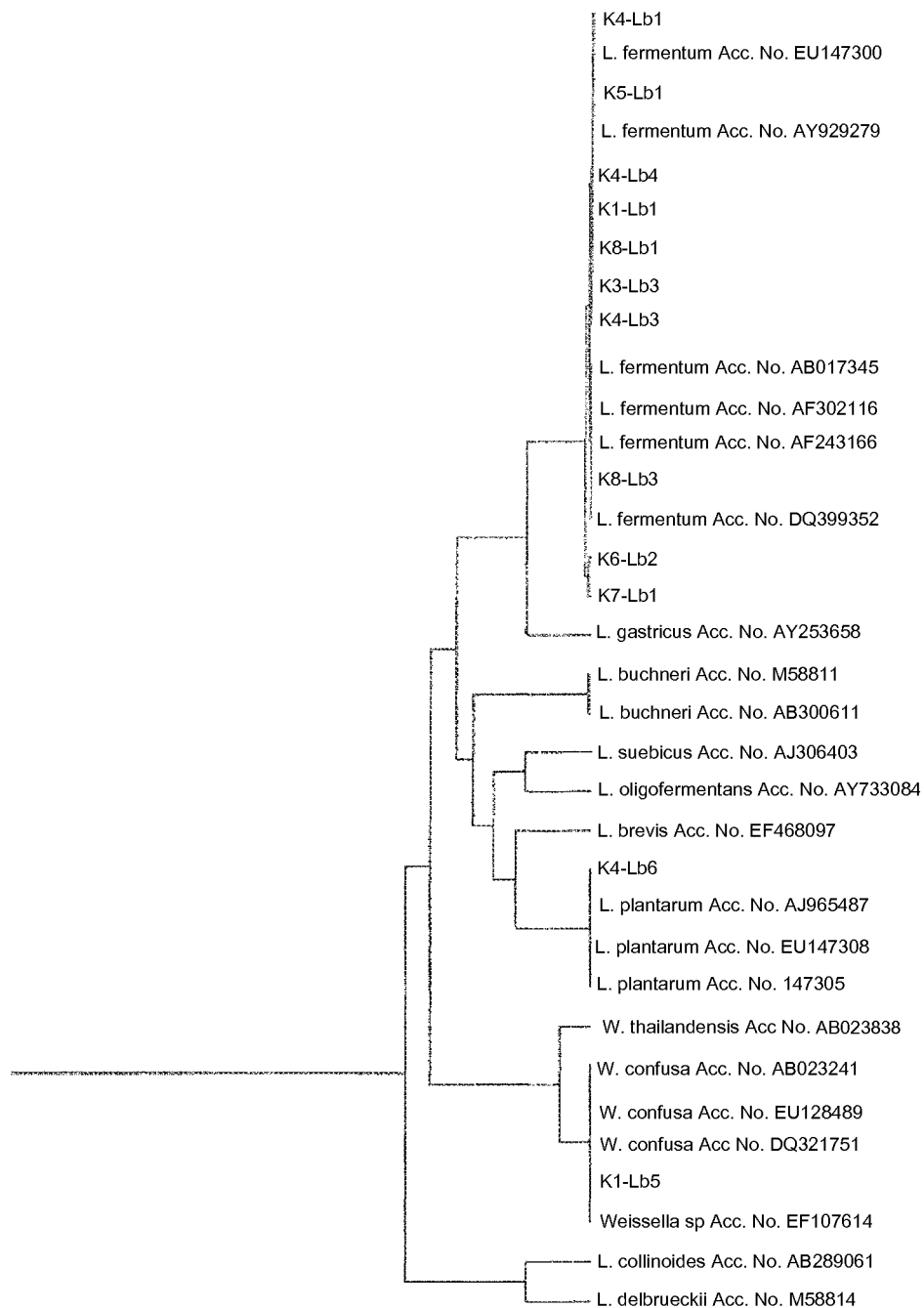
Figure 3:
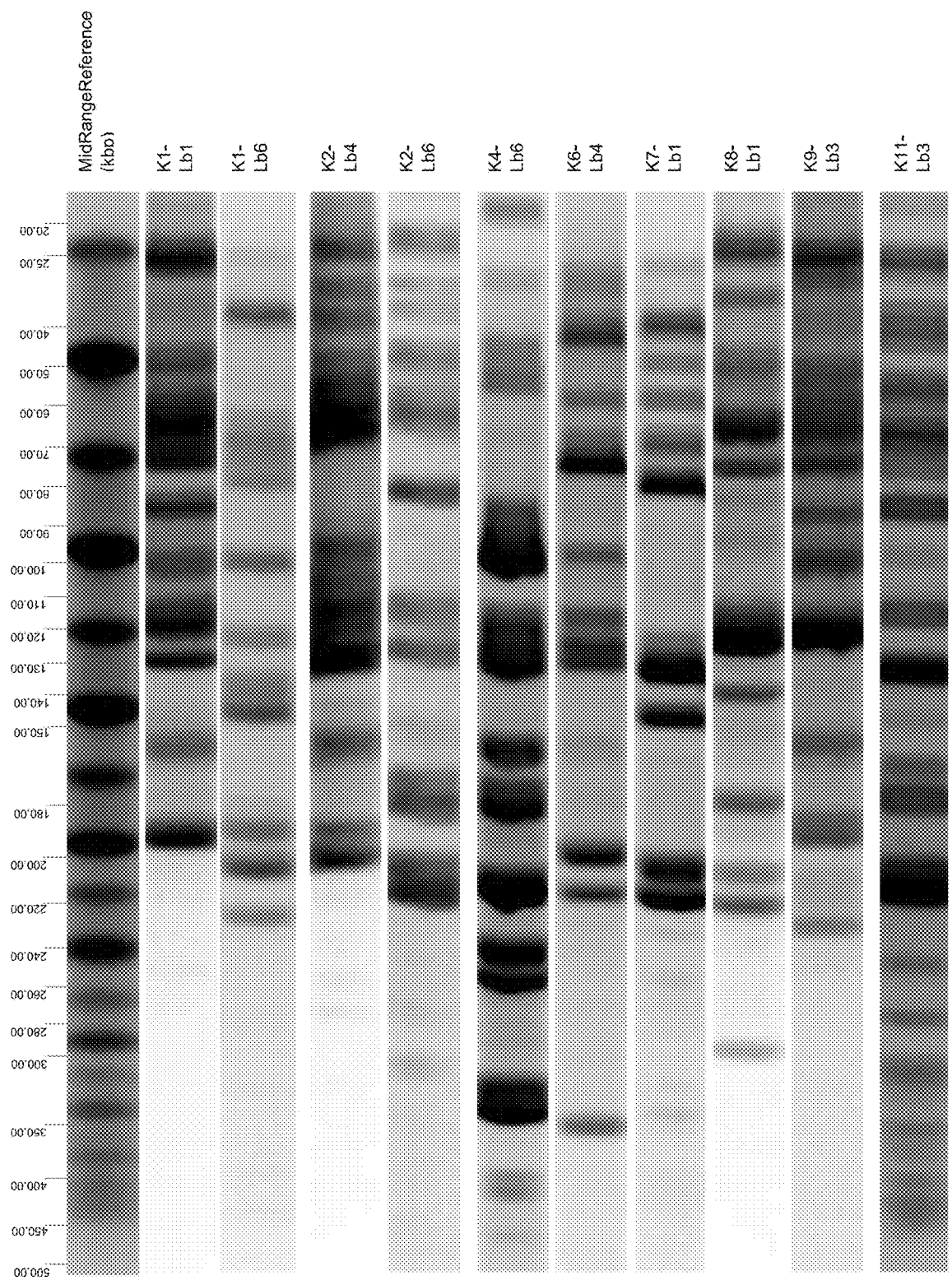
Figure 4A:
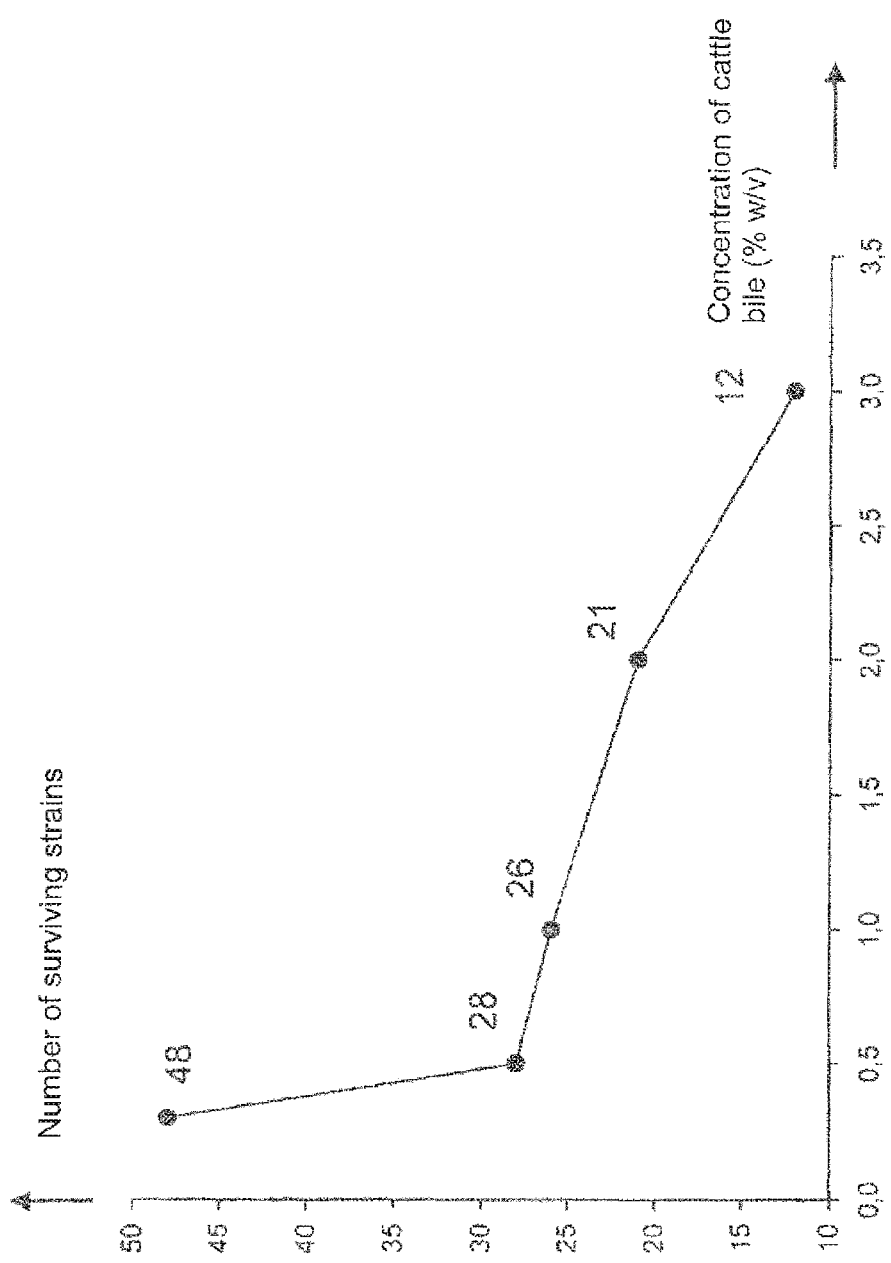
FIGS. 4A to 4C show the tolerance of the strains to bile salt.
Figure 4B:
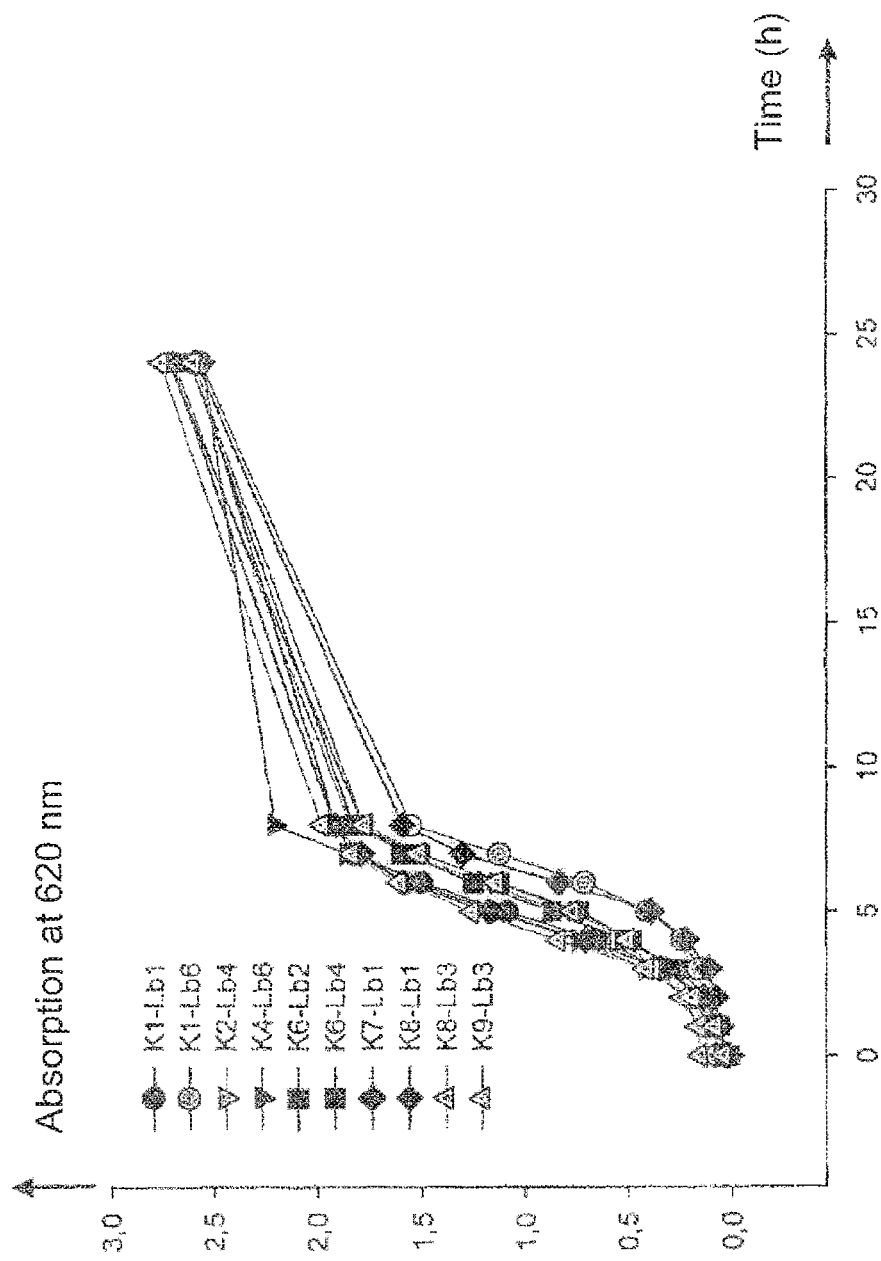

In FIG. 4B, by measurement of the absorption of the samples at 620 nm, the specific growth of the strains in 0.3% cattle bile solution is plotted against time. A somewhat similar behaviour is shown for all strains.

Figure 4C:
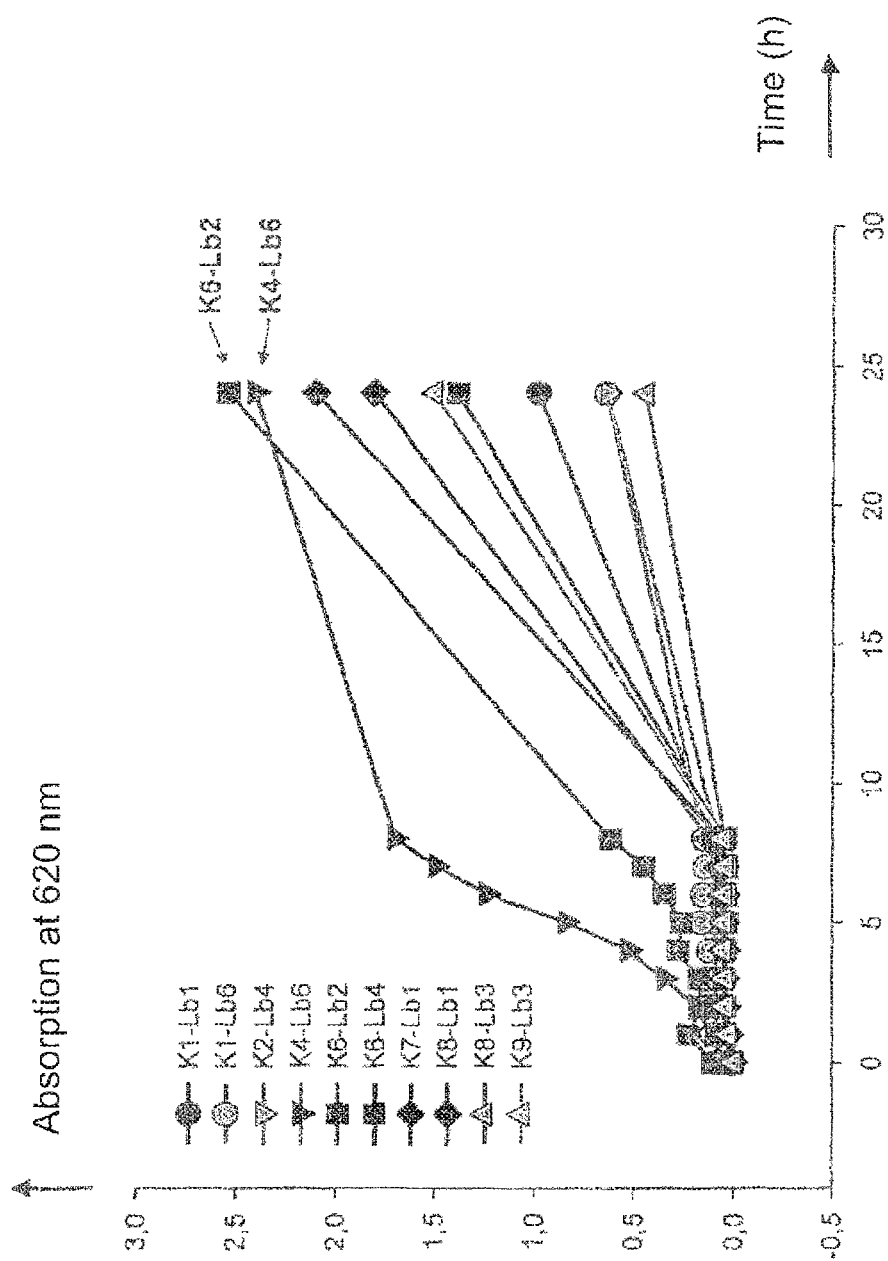

FIG. 4C shows the results of an, in principle, identical measurement, but with 3.0% concentration of cattle bile. A particularly rapid growth of the strain K4-Lb6 (deposition number DSM 22830), which is very obviously highly robust with respect to bile salt, is shown here.

Figure 5:
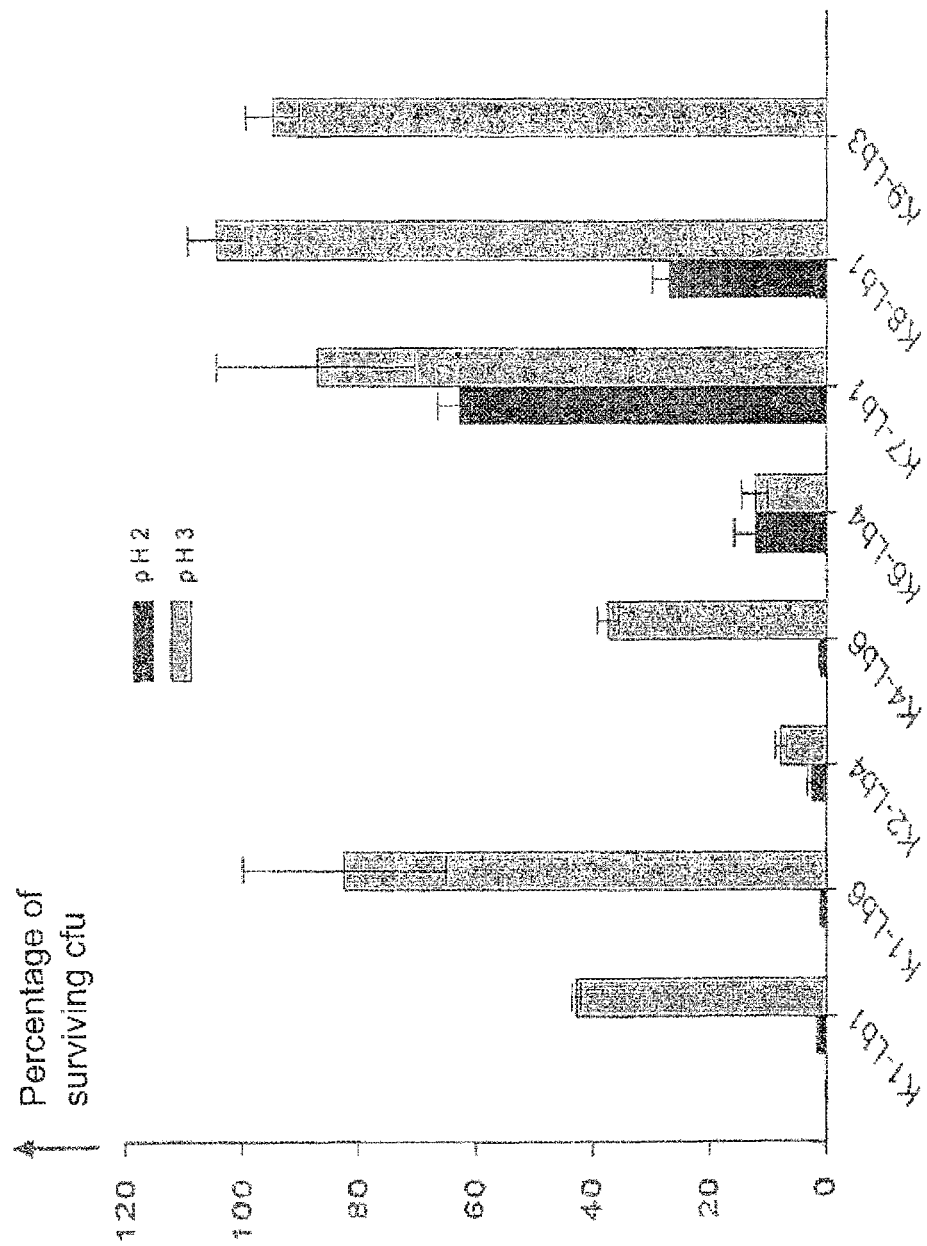

In FIG. 5, the resistance of the strains to very acid milieu is shown, specifically for pH 2 and pH 3. The cells were incubated in 0.35% NaCl (containing 3 g l<−1> pepsin) and adjusted to pH values of 2, 3 and 6.5 for 3 h at 37[deg.] C. in each case. The surviving cells were counted on an MRS agar plate at 37[deg.] C. for 48 to 72 h. The values at pH 6.6 defined as reference value with 100% and the cells surviving at pH 2 and pH3 were compared with this reference value.

Figure 6A:
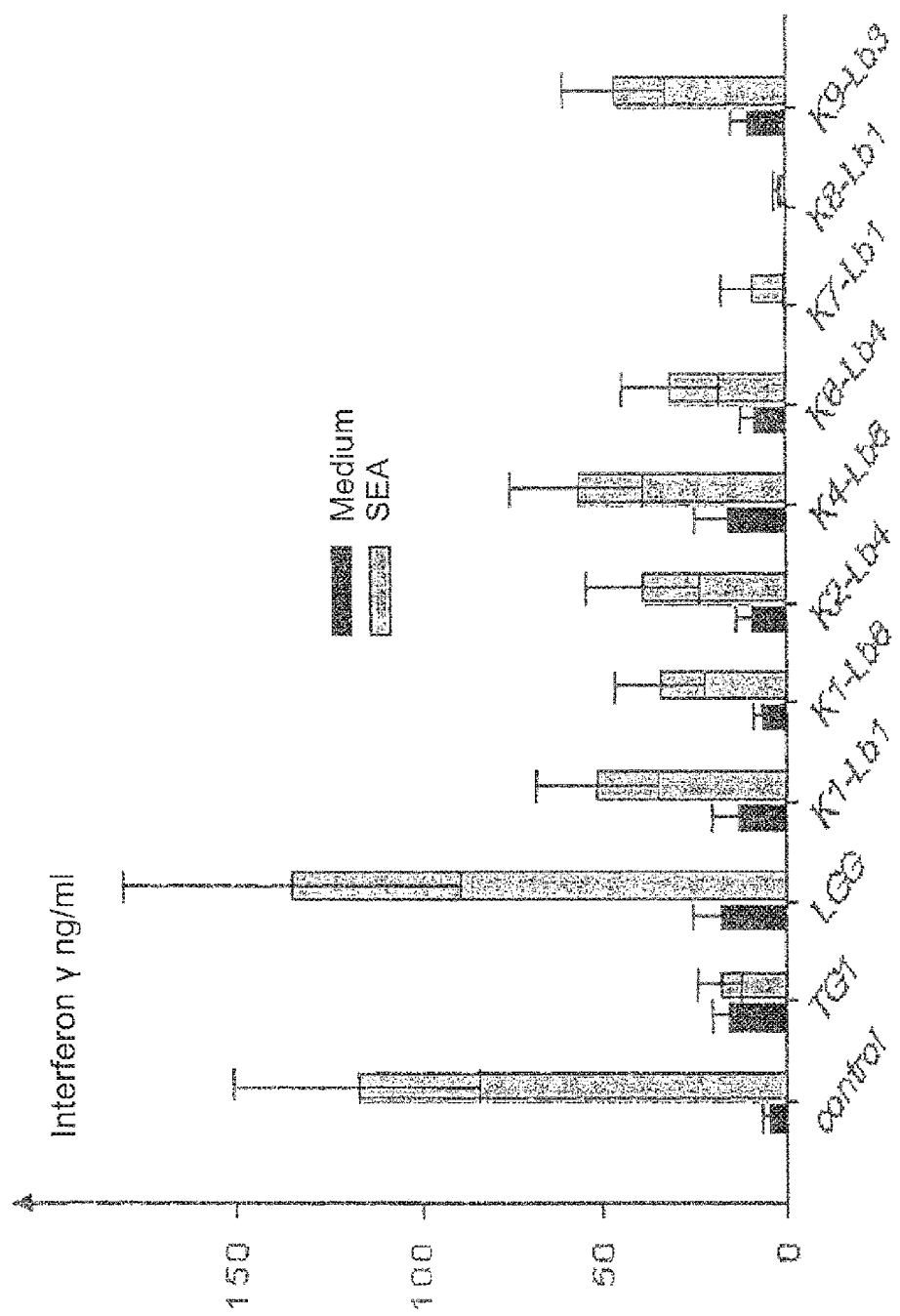
Figure 6B:
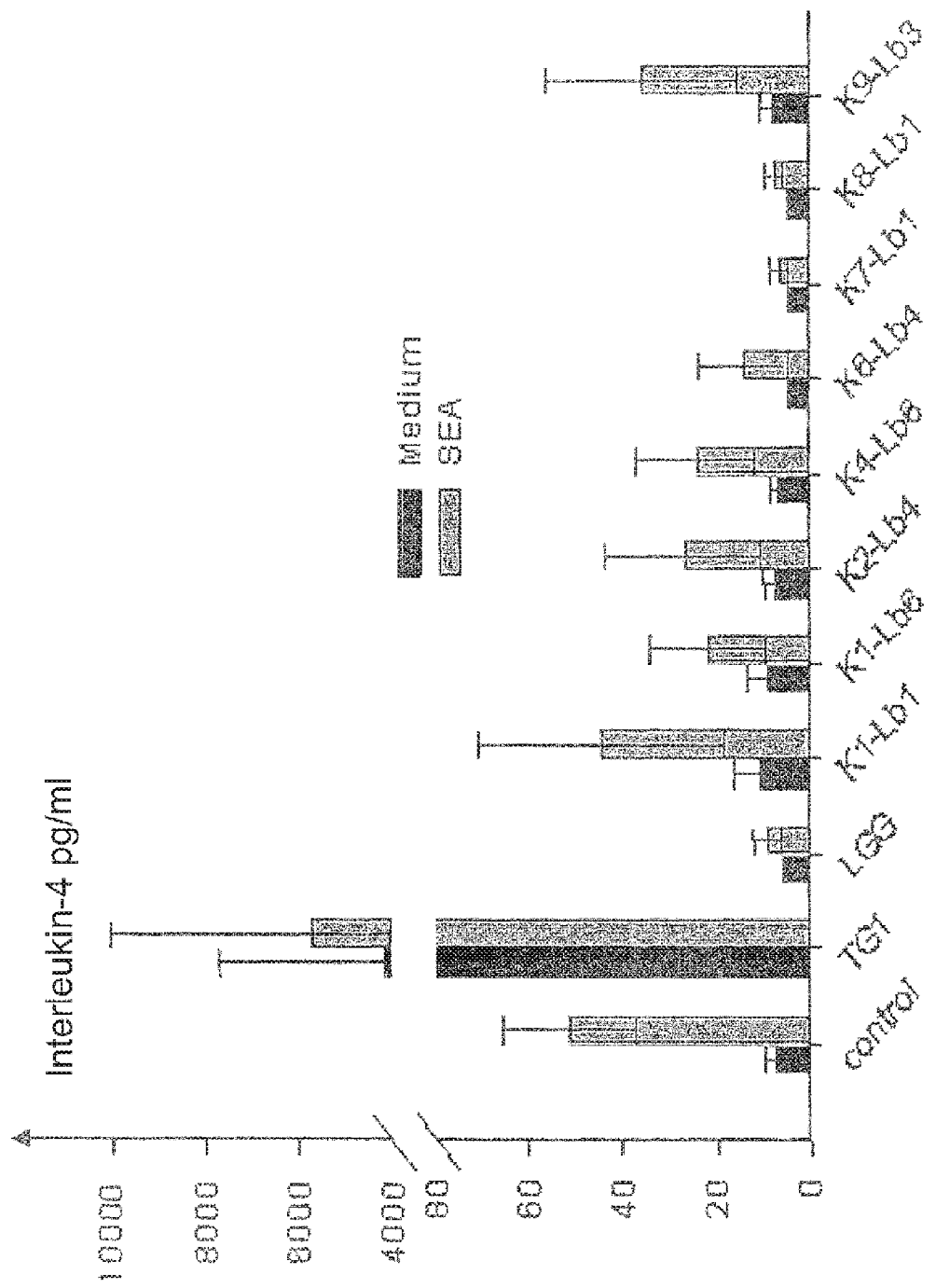

FIGS. 6A to 6C show Th1 and Th2 cytokine production of human blood cells (PBMCs) after co-incubation in vitro with Kimere Lactobacilli strains, specifically with and without stimulation by superantigenic *Staphylococcus* enterotoxin A (SEA). As an effect of the bacterial strains on the immune system and on the shift of the Th1/Th2 ratio, FIG. 6A shows the production of interferon-[gamma] and FIG. 6B shows the production of interleukin-4 and FIG. 6C shows the resulting ratio of interferon-[gamma] and interleukin-4.

What is claimed is:

1. A method of strengthening the immune system in a human comprising: administering a composition comprising one or more isolated bacterial strains from Kimere to a human orally, wherein the isolated bacterial strains are strains of *Lactobacillus fermentum* and/or *Lactobacillus plantarum*, and wherein the administration of the composition provides an immunomodulating effect in the human, wherein the one or more strains are selected from:

*Lactobacillus fermentum* K1-Lb1 (deposition number DSM 22837), or

*Lactobacillus plantarum* K4-Lb6 (deposition number DSM 22830), wherein the administration of K1-Lb1 or K4-Lb6 changes the Th1/Th2 balance towards Th1;

*Lactobacillus fermentum* K7-Lb1(deposition number DSM 22831), or

*Lactobacillus fermentum* K8-Lb1 (deposition number DSM 22832), wherein the administration of K7-Lb1 or K8-Lb1 changes the Th1/Th2 balance towards Th2, or

*Lactobacillus fermentum* K2-Lb6 (deposition number DSM 22829), or

*Lactobacillus fermentum* K11-Lb3 (deposition number DSM 22838), wherein the administration of K2-Lb6 or K11-Lb3 increased the release of defensin from intestinal cell.

2. The method according to claim 1, wherein the isolated bacterial strains tolerate up to 0.3% (w/v) of bile acid.

3. The method according to claim 1, wherein the isolated bacterial strains are selected from

*Lactobacillus fermentum* K7-Lb1, or

*Lactobacillus fermentum* K8-Lb1, or

*Lactobacillus plantarum* K4-Lb6 wherein the strain K4-Lb6 tolerates up to 3.0% (w/v) of bile acid and the strains K7-Lb1 and K8-Lb1 show survival rates of over 80% at a pH of 3.

4. A method of strengthening the immune system in a human comprising:

administering a composition comprising one or more isolated bacterial strains from Kimere to a human orally, wherein the isolated bacterial strains are strains of *Lactobacillus fermentum* and/or *Lactobacillus plantarum*, and wherein the administration of the composition provides an immunomodulating effect in the human, wherein the one or more strains are selected from:

*Lactobacillus fermentum* K11-Lb3 (deposition number DSM 22838), of

*Lactobacillus fermentum* K7-Lb1(deposition number DSM 22831), or

*Lactobacillus fermentum* K8-Lb1 (deposition number DSM 22832), wherein the immune system is strengthened by an inhibition of inflammations.

* * * * *

UNITED STATES PATENT AND TRADEMARK OFFICE
CERTIFICATE OF CORRECTION

| | | |
|---|---|---|
| PATENT NO. | : 11,667,977 B2 | |
| APPLICATION NO. | : 14/708942 | |
| DATED | : June 6, 2023 | |
| INVENTOR(S) | : Jurgen Schrezenmeir and Knut Heller | |

It is certified that error appears in the above-identified patent and that said Letters Patent is hereby corrected as shown below:

On the Title Page

Assignee Item (73), add "SLIMBIOTICS GMBH, Vienna (AT)"

Signed and Sealed this
Fourth Day of July, 2023

Katherine Kelly Vidal
*Director of the United States Patent and Trademark Office*